United States Patent
Corey Jr. et al.

[19]

[11] Patent Number: 5,899,425

[45] Date of Patent: May 4, 1999

[54] ADJUSTABLE SUPPORTING BRACKET HAVING PLURAL BALL AND SOCKET JOINTS

[75] Inventors: Edmund R. Corey Jr., Schwenksville; John A. Fanticola, Jr.; William H. Pilling, both of North Wales; Gerald A. Powell, Havertown, all of Pa.; David E. Weston, Rockford, Mich.; Robert W. Wilson, Dresher, Pa.

[73] Assignees: Medtronic, Inc., Minneapolis, Minn.; Pilling Weck Incorporated, Ft. Washington, Pa.

[21] Appl. No.: 09/071,701

[22] Filed: May 1, 1998

Related U.S. Application Data

[60] Provisional application No. 60/045,484, May 2, 1997.

[51] Int. Cl.⁶ .................................................. A61B 17/00
[52] U.S. Cl. ................................ 248/276.1; 248/288.51; 248/316.4; 600/229; 403/56
[58] Field of Search ................................ 248/276.1, 160, 248/288.51, 316.4, 231.41, 231.71, 279.1; 600/229; 403/56

[56] References Cited

U.S. PATENT DOCUMENTS

| | | |
|---|---|---|
| D. 293,470 | 12/1987 | Adler . |
| D. 389,913 | 1/1998 | Bookwalter et al. . |
| 870,429 | 11/1907 | Grimler . |
| 1,279,803 | 9/1918 | Watson . |
| 2,510,198 | 6/1950 | Tesmer ................................... 248/160 |
| 3,096,962 | 7/1963 | Meijs ................................. 248/276.1 |
| 3,168,274 | 2/1965 | Street ................................ 248/160 X |
| 3,529,797 | 9/1970 | Street .................................... 248/160 |
| 3,584,822 | 6/1971 | Oram . |
| 3,858,578 | 1/1975 | Milo ...................................... 600/229 |
| 4,461,284 | 7/1984 | Fackler . |
| 4,867,404 | 9/1989 | Harrington et al. . |
| 4,898,490 | 2/1990 | Herbermann et al. . |
| 4,949,927 | 8/1990 | Madocks et al. ....................... 248/160 |
| 5,020,933 | 6/1991 | Salvestro et al. . |
| 5,284,130 | 2/1994 | Ratliff .................................... 600/229 |
| 5,348,259 | 9/1994 | Blanco et al. ...................... 403/56 X |
| 5,447,149 | 9/1995 | Kikawada et al. ..................... 600/229 |
| 5,513,827 | 5/1996 | Michelson ........................... 248/279.1 |
| 5,727,569 | 3/1998 | Benetti et al. . |

*Primary Examiner*—Derek J. Berger
*Assistant Examiner*—Stephen S. Wentsler
*Attorney, Agent, or Firm*—Howson & Howson

[57] ABSTRACT

An articulating supporting bracket for a surgical tissue stabilizer comprises a series of elements joined to one another by articulating ball-and-socket joints. A flexible cable extends through passages in the elements, and, when tightened, causes the balls and sockets to lock together frictionally. The ball of each joint fits into its socket by an interference fit, whereby the ball and socket of each joint engage one another over an area of contact when the cable is tightened, thereby providing a strong, rigid support for the tissue stabilizer.

15 Claims, 4 Drawing Sheets

ADJUSTABLE SUPPORTING BRACKET HAVING PLURAL BALL AND SOCKET JOINTS

CROSS REFERENCE TO RELATED APPLICATION

This claims the benefit of our co-pending provisional application Ser. No. 60/045,484, filed on May 2, 1997.

SUMMARY OF THE INVENTION

This invention relates to supports, and more particularly to improvements in adjustable supporting brackets, having plural ball and socket joints, which form lockable, articulating arms for holding surgical instruments or for similar purposes.

In surgery, it is common practice to mount adjustable supporting brackets on a side rail of an operating table to support retractors, endoscopes and other surgical devices. Similar adjustable brackets are used to support lamps, measuring instruments for machine tools, and various other devices.

Recent developments in heart surgery have necessitated stronger and more rigid adjustable brackets. In particular, a procedure has been introduced for carrying out cardiac bypass surgery without stopping the patient's heart. In this procedure, a device, known as a "tissue stabilizer," having an array of small suction cups, is used. The tissue stabilizer is attached to the wall of the heart by drawing a vacuum in the suction cups. With one or more such devices attached to the wall of the heart, the site at which the repair is to take place can be held fixed, while the heart continues to beat.

The successful use of the tissue stabilizer requires a supporting bracket which is easily adjustable and unobtrusive. More importantly, however, it requires the bracket to be very strong and rigid so that the tissue stabilizer can immobilize the portion of the heart wall on which the surgeon is working, to allow the surgeon to make the necessary incisions and sutures to graft one or more bypass vessels into place.

An ideal way to support the tissue stabilizer is to use a lockable articulating arm. Examples of lockable articulating arms particularly designed for use with surgical instruments are described in the following U.S. patents: Harrington et al. 4,867,404, Fickler 4,461,284, Salvestro et al. 5,020,933, Blanco et al. 5,348,259 and Michelson 5,513,827. Other, similar articulating arms, for holding measuring instruments, lamps, and various other articles are described in the following U.S. patents: Grimler 870,429, Watson 1,279,803, Meijs 3,096,962, Street 3,529,797, Oram 3,584,822, Herbermann et al. 4,898,490 and Madocks et al. 4,949,927. A number of these devices utilize a series of elements joined to one another by articulating ball-and-socket joints, a cable extending through passages in the elements, and a device for tightening the cable and thereby causing the balls and sockets to lock together frictionally. These ball-and-socket joints fall into three general categories.

In one category, the ball is engaged by the relatively sharp, circular edge of a socket, the sharp edge biting into the ball along a circular line of contact when the cable is pulled tight, as in Meijs U.S. Pat. No. 3,096,962, and Street U.S. Pat. No. 3,529,797. The device of Blanco et al. U.S. Pat. No. 5,348,259 is similar, but utilizes teeth in the socket.

In a second category, the balls engage frusto-conical socket surfaces along a circular line of contact. Devices in this category are described in Watson U.S. Pat. No. 1,279,803, Madocks et al. U.S. Pat. No. 4,949,927 and Oram U.S. Pat. No. 3,584,822. The device of Salvestro et al. U.S. Pat. No. 5,020,933 is similar, but eliminates the cable by providing frusto-conical locking devices which engage opposite sides of each ball.

In a third category, exemplified by Grimler U.S. Pat. No. 870,429 and Michelson U.S. Pat. No. 5,513,827, the balls are engaged by conforming spherical socket surfaces over limited areas of contact. In the case of Michelson, the contact area for each ball is approximately 20% of the total surface area of a sphere having the same diameter as the ball. In Grimler, the ratio of the contact area to the total sphere is only about 10%.

Because the ball and socket joints of the lockable articulating arms of the prior art utilize line contact, or at most, contact over a very limited area, in general they either have limited strength and rigidity, or are bulky or require excessive tightening force. Because of these characteristics, the articulating arms of the prior art are not ideally suited for supporting tissue stabilizers for heart surgery.

The principal object of this invention is to provide a supporting bracket made up of articulating ball-and-socket joints, which is sufficiently strong and rigid to be ideally suited for supporting a tissue stabilizer for heart wall immobilization. Among the other objects of the supporting bracket in accordance with the invention are structurally simplicity, ease of use, unobtrusiveness, versatility, flexibility and reliability.

Briefly, the supporting bracket in accordance with the invention is a multiple link, flexible ball and socket arm, lockable in any desired position by tightening an internal tensioning cable. Although is intended primarily for supporting a tissue stabilizer used to immobilize portions of the heart during cardiac artery surgery, but can be used for various other purposes.

The bracket is characterized by an interference fit between the spherical balls and their sockets. The diameter of each ball is preferably approximately $\frac{1}{1000}$ to $\frac{2}{1000}$ inch larger than the diameter of the socket into which it fits. The sockets are hemispherical or almost hemispherical, and their walls are sufficiently flexible to allow the balls to enter them The very small difference in diameter, and the flexibility of the socket walls, allows the balls and sockets to be engaged over an area of contact. The terms "area of contact" and "area contact," as used herein, mean contact between a ball and a socket over a substantial area in a common sphere, greater than approximately 20% of the total surface area of the sphere, and is distinguishable from "line contact," which is contact between a ball and socket over a circular line or a narrow band having an area which is substantially less than 20% of the total area of the sphere corresponding to the larger of the ball or socket. The area of contact extends from the periphery of the socket to the envelope of the perimeter of the cable opening in the concave spherical surface and the circle defining the end of the convex spherical surface adjacent to the cable opening therein. The contact area is preferably approximately 30% to 40% of the total surface area of a corresponding sphere. The ball and socket elements vary in size along the length of the arm so that the arm is tapered.

Other objects, details and advantages of the invention will be apparent from the following detailed description when read in conjunction with the drawings.

DETAILED DESCRIPTION

Figure 1:
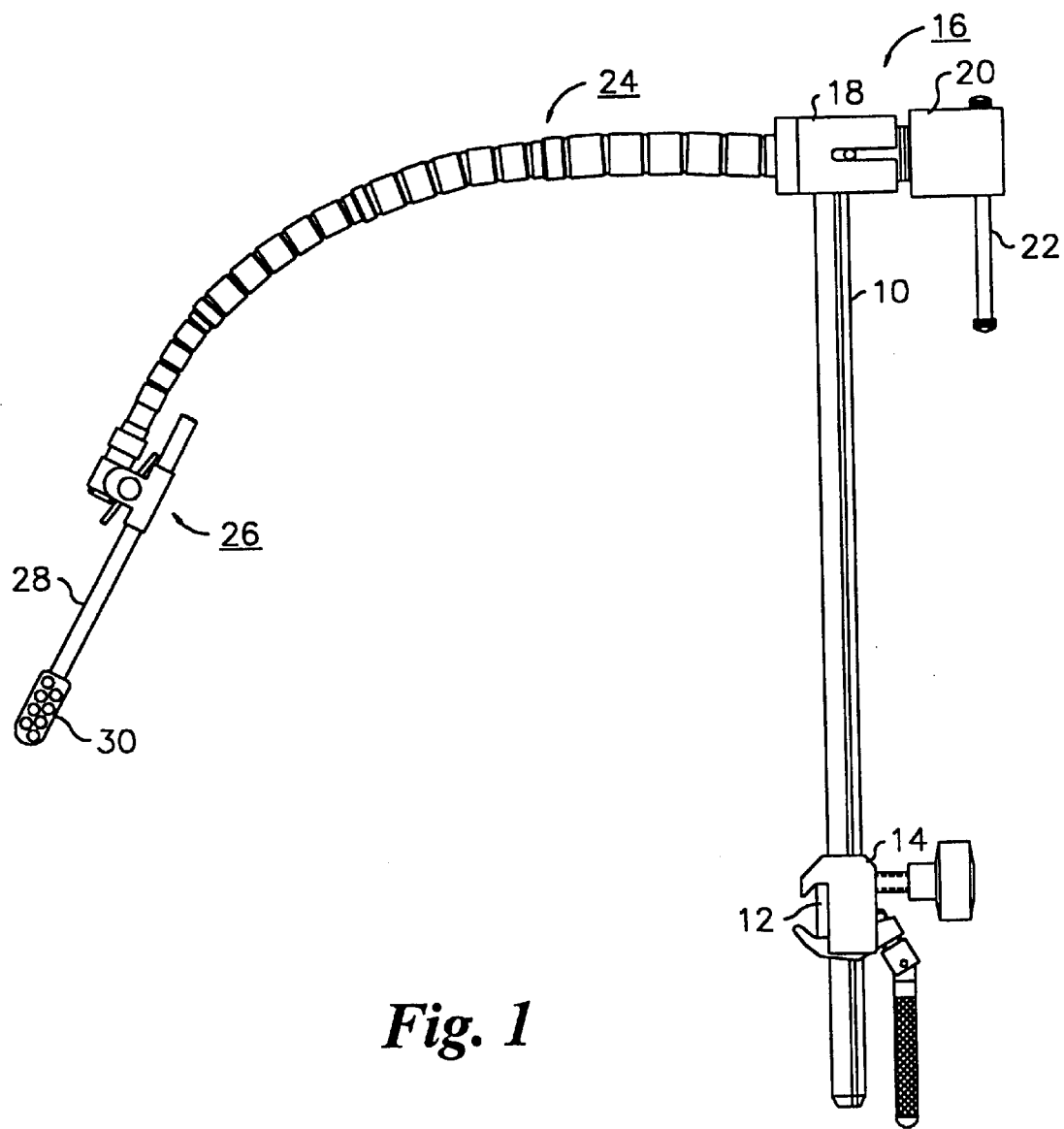
FIG. 1 is an elevational view showing an tissue stabilizer supported from the side rail of an operating table by the bracket in accordance with the invention.

The assembly shown in FIG. 1 comprises a vertical post 10 attached to the side-rail 12 of an operating table (not shown) by a clamp 14. The post preferably has plural facets, which cooperate with the clamp to prevent rotation of the post relative to the clamp. Depth markings (not shown) are also provided on the post to facilitate height adjustment. A tensioner 16, mounted at the top of the post, comprises a mounting block 18 and a rotatable member 20 having a transversely slidable crank arm 22.

Connected to the side of the mounting block 18 opposite to the side having the rotatable member 20, is one end of a flexible arm 24 comprising a series of articulating elements connected to one another by ball-and-socket joints. The flexible arm 24 has a clamp assembly 26 mounted at its other end. The clamp assembly 26 holds the shank 28 of a tissue stabilizer 30.

Figure 2:
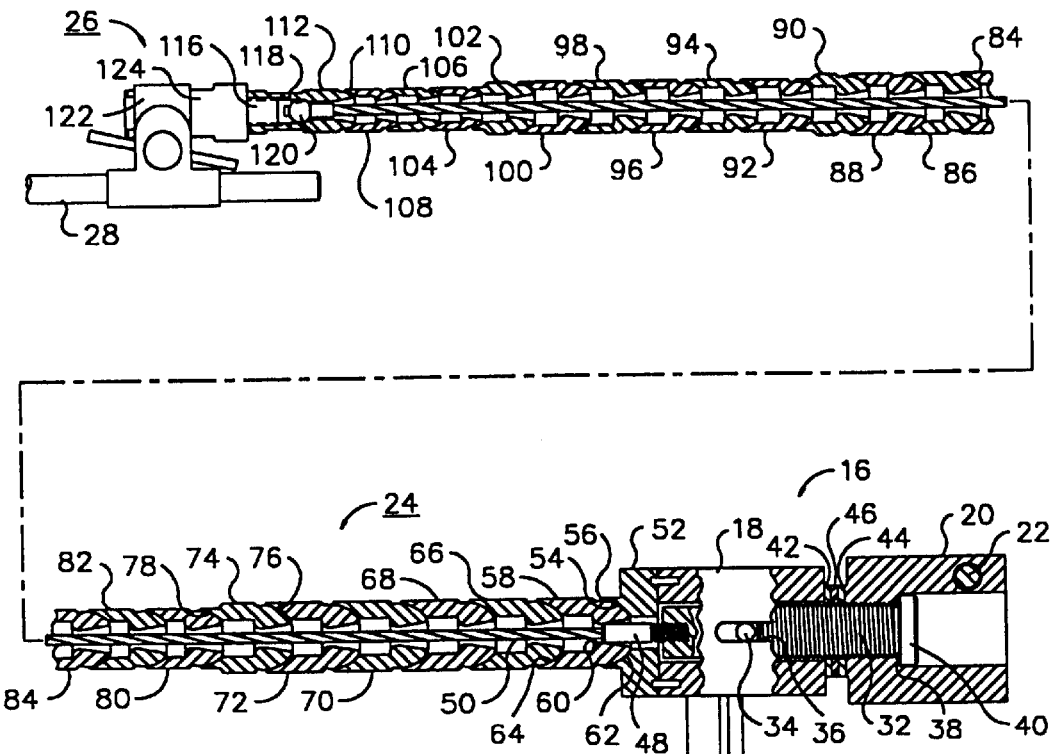
FIG. 2 is a longitudinal section showing the ball-and-socket elements of the bracket, together with the cable, the cable tightening mechanism and its supporting post, and a clamp at the distal end of the bracket.
Figure 2:
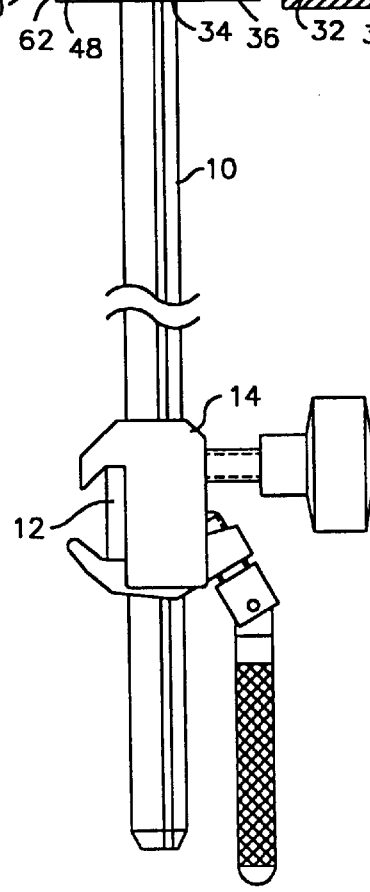

FIG. 2 shows that the tensioner mounting block 18 has an internal passage receiving a screw 32. Affixed to the screw is a transverse pin 34, which rides in slots formed in opposite sides of the mounting block, one such slot being shown at 36. The engagement of the pin with the slots prevents the screw from rotating relative to mounting block 18. The threads of the screw 32 engage internal threads in a rotatable member 20, which also has an internal shoulder 38 engageable with head 40 of the screw.

Between the block 18 and the rotatable member 20, and surrounding the screw 32, is a thrust bearing comprising a pair of stainless steel washers 42 and 44 on opposite sides of a Nylon ball cage 46.

A pin 48, attached to one end of a flexible tensioning cable 50, is threaded into the end of the screw 32. The cable is typically a ⅛ inch diameter, multi-strand, stainless steel cable.

Figure 3:
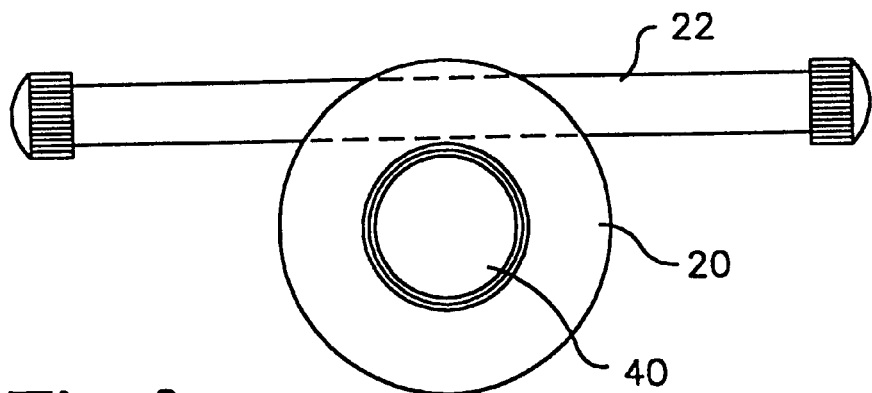
FIG. 3 is an end elevation of the cable tightening mechanism, as seen from the right side of FIG. 1.

As shown in FIG. 3, crank arm 22 is mounted in a transverse hole in member 20, so that member 20 can be conveniently rotated manually, and so that the torque applied to the rotating member can be increased, when necessary, by sliding the crank to one side. As will be apparent from an inspection of the tensioner assembly as shown in FIG. 2, clockwise rotation of member 20 (as seen from the right) will exert a pulling force on cable 50. The relationship between cable tension and the torque applied to member 20 depends primarily upon the pitch of the threads of screw 32 and on thread friction. Preferably, the pitch of the threads of screw 32 is selected so that 14 ft. lb. of torque exerted on member 20 will apply about 1000 pounds of tension to the flexible cable. A typical tension in the cable is about 1250 pounds. The length of the crank arm 22 should be such that, by appropriate adjustment, any surgeon or operating room assistant will be able to exert 14 ft. lb. of torque.

A socket member 52 is secured to the end wall of block 18 by pins. The socket member has a concave spherical surface 54 extending from a circular edge 56, which is concentric with the spherical surface, to the end opening of a passage in element 58 through which the cable end pin 48 extends.

The flexible, articulating arm 24, as shown in FIG. 2, comprises a series of elements, preferably made of stainless steel. Each element has an internal passage for accommodating the cable 50. Each element has a convex, spherical surface at one end and a concave, spherical surface at the other end. For example, element 58 has an internal passage 60, a convex spherical surface 62 and a concave spherical surface 64. The convex surface 62 is in mating relationship with the concave surface 54 of member 52.

Element 58 is followed by a series of elements 66, 68, 70 and 72, each of which is identical to element 58. The convex spherical surface of each of element 66–72 in the series is in mating relationship with the concave spherical surface of an adjacent element in the series. In a preferred embodiment, both the convex and the concave spherical surfaces of elements 58 and 66–72 have a nominal diameter of 0.875 inch.

A transition element 74 has a convex spherical surface 76 having a nominal diameter of 0.875 inch, mating with the concave spherical surface of element 72. The concave surface 78 of transition element 74 is smaller, having a nominal diameter of 0.750 inch. It mates with the convex surface of a first element 80 of a series of identical mating elements 80, 82, 84, 86 and 88 each having convex and concave surfaces with a nominal diameter of 0.750 inch. Another transition element 90, having a 0.750 inch convex surface and a 0.625 concave surface, connects to the first element 92 of a series of five identical elements 92, 94, 96, 98 and 100, each having convex and concave surfaces with a nominal diameter of 0.625 inch. Another transition element 102, having a 0.625 inch convex surface and a 0.500 concave surface, connects to the first element 104 of a final series of three identical elements 104, 106 and 108, each having convex and concave surfaces with a nominal diameter of 0.500 inch.

The last element 108, has its concave spherical surface in mating relationship with a convex spherical surface 110 of a fitting 112, which is connected to clamp assembly 26. Fitting 112 has an internal passage 116, with a shoulder 118 engageable with a ball 120 secured to the distal end of cable 50.

The use of elements of progressively decreasing size, proceeding form the proximal toward the distal end of the arm, results in a tapered arm in which the elements near the distal end are lighter in weight and less obtrusive to the surgeon, while the elements near the proximal end of the arm, which are subjected to a greater torque from forces applied to the distal end, are larger in diameter, and better able to resist articulating movement.

Figure 4:
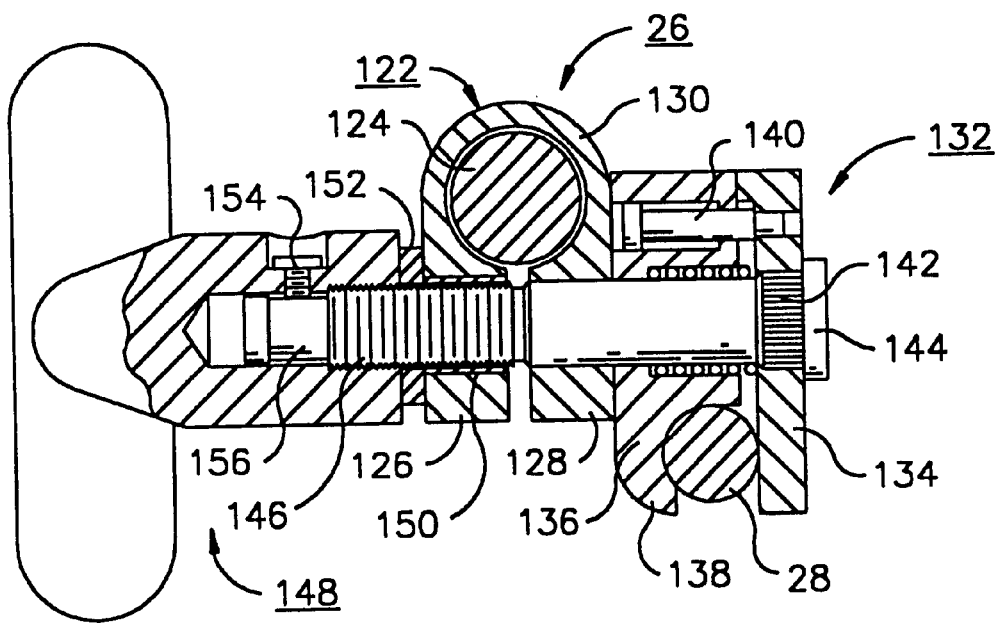
FIG. 4 is a sectional view showing details of the distal end clamp assembly.

As shown in FIG. 4, the clamp assembly 26 comprises a flexible U-clamp 122, which grips a cylindrical extension 124 secured to the fitting 112 at the distal end of the arm 24. The U-clamp is a unitary element consisting of two opposed body parts, 126 and 128, connected to each other by an thin, flexible arcuate member 130, which extends almost all the way around extension 124. The length of the arcuate member 130 is such that the body parts 126 and 128 are slightly separated from each other.

Next to body part 128 of the U-clamp is a clamp 132 comprising a plate 134 and an opposed member 136, the latter having an arcuate clamping face 138 adapted to engage shank 28 of the tissue stabilizer. A pin 140, secured to plate 134, extends into, and is slidable in, a passage in member 136.

Both the U-clamp and clamp 132 are mounted on a rod 142, which has a head 144 in engagement with an outer face of plate 134. The rod has threads 146, which are engaged by internal threads at one end of a wing nut 148. The threads 146 extend into body part 126 of U-clamp 122, and a thin-walled sleeve 150 is fitted into body part 126 to minimize the clearance between the threads and the body part. This prevents the threads from jumping over the edge of the opening of the body part as the wing nut is tightened, and achieves a smooth clamping action.

A washer 152 is situated between the wing nut 148 and U-clamp 122 to distribute the thrust exerted by the wing nut. Inside the wing nut, a set screw 154 extends into an axially elongated groove 156 in rod 142 to prevent accidental removal of the wing nut from rod 142 while permitting the wing nut to move a through a limited distance along threads 146.

Because of the flexibility of U-clamp 122, as the wing nut 148 is tightened, the clamp 132 first grips the shank 28 of the tissue stabilizer. As the wing nut is further tightened, clamp 122 grips extension 124 of arm 24. This allows the surgeon to adjust the tissue stabilizer relative to the clamp assembly, and thereafter rotate the clamp assembly about extension 124 and lock it in a fixed position. Thus, the freedom of movement of the tissue stabilizer can be reduced in steps, by manipulating only a single tightening device, namely the wing nut.

Figure 5:
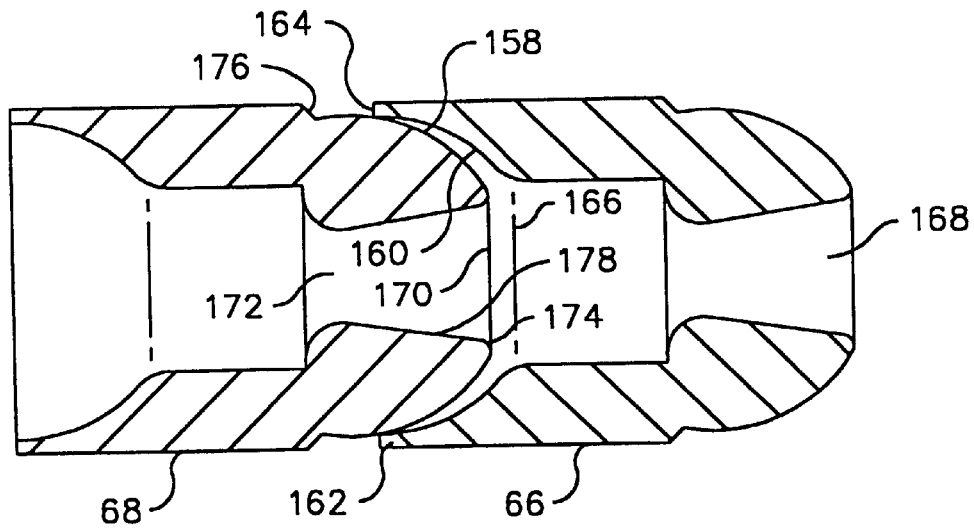
FIG. 5 is an enlarged sectional view through two of the adjoining elements of the bracket, showing the elements in their loosened condition.
Figure 6:
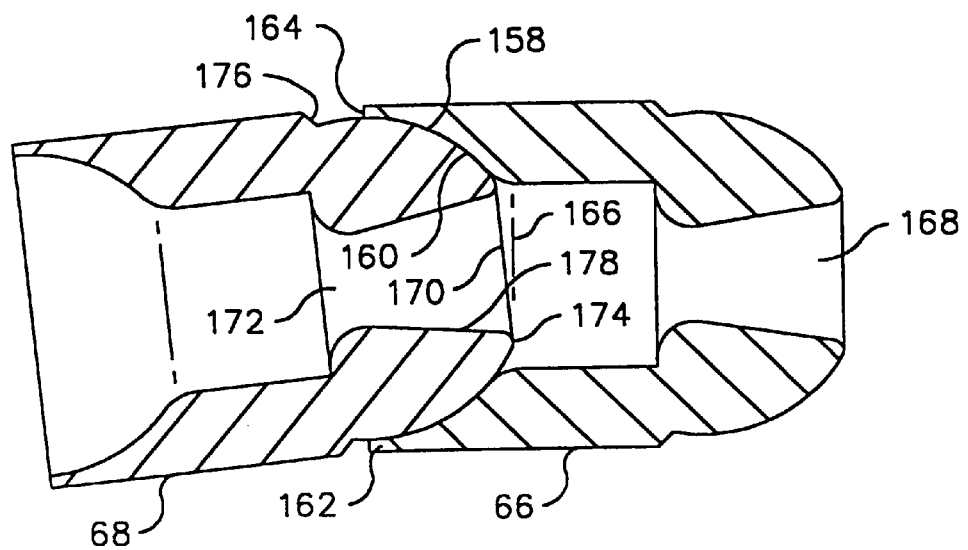
FIG. 6 is an enlarged sectional view, similar to FIG. 5, but showing the same elements in their locked condition.

FIGS. 5 and 6, show two identical articulating elements 66 and 68, of arm 24, loosely engaged with each other. The spherical convex surface 158, which has a nominal diameter of 0.875 inch, preferably has an actual diameter of 0.876 inch, while the spherical concave surface with which it is engaged, surface 160 of element 66, which also has a nominal diameter of 0.875 inch, has an actual diameter, when relaxed, of 0.8745 inch. Thus, the diameters of the two spherical surfaces are different by 0.0015 inch, the convex sphere being larger. The spheres fit together, as shown in FIG. 6, by an interference fit. The wall 162 of element 66 is sufficiently thin and resilient to allow the two surfaces 158 and 160 to come together in area contact with each other. The circular edge 164 of the opening of element 66 is preferably concentric with the center of the imaginary sphere in which surface 160 lies. This center is a common center for both spherical surfaces 158 and 160 when the elements are fully engaged with each other. The contact area of the two spherical surfaces extends from a first circle, defined by edge 164, to the envelope defined by the perimeter of end opening 166 of passage 168 and a second circle, adjacent to the end opening 170 of passage 172, where the convex spherical surface 158 meets a rounded edge 174 of end opening 170. The edge 174 is rounded to avoid a sharp edge that could damage the cable 50. The rounded edge has a very small radius of curvature to maximize the contact area of the mating convex and concave surfaces, and the fact that the edge is rounded instead of sharp makes only a negligible difference so far as the contact area is concerned.

Generally, when the axes of the passages of the two adjoining elements are aligned, the perimeter of the opening 166 and the second circle adjacent to the rounded end opening of the convex spherical surface will substantially coincide, as shown in FIG. 5. However, when the one element is tilted relative to the other, the envelope of the perimeter of end opening 166 and the second circle will take the form of the outline of two intersecting circles lying in planes that are slightly oblique to each other. The tilting of one of two adjoining elements relative to the other slightly decreases the contact area between their mating spherical surfaces.

The contact area is preferably at least approximately 30% of the total surface area of a corresponding sphere, and, in a practical arm, will be in the range from approximately 30% to 40% of the total surface area of a corresponding sphere.

As shown in FIG. 6, the outer surface of element 68 has a shoulder 176, which is engageable by edge 164 of element 66 to limit the angle of articulation of the two elements. The angle is preferably limited to approximately 15°. The convex spherical part of element 68 is sufficiently thick to avoid deformation the convex spherical surface, and passage 172 is flared at 178, so that, even when the two elements are disposed at the maximum 15° angle relative to each other, the cable is not pinched.

The difference between the diameters of the convex spherical surfaces and their mating concave surfaces can vary somewhat, depending on the nominal diameters of the surfaces. For example, the nominally 0.500 inch convex surface can have a diameter that is 0.002 inch greater than that of the nominally 0.005 inch diameter concave surface. On the other hand, because of their greater contact area, the nominally 0.875 inch convex and concave surfaces can differ in diameter by a lesser amount, e.g. 0.0015 inch, or even 0.001 inch, and still have adequate resistance to relative rotation when pulled together by the cable. Thus, to achieve satisfactory strength along the length of the articulating arm, the convex and concave parts of the joints should have a progressively greater difference in diameter as the joints become smaller. That is, for any two joints of different size, the ball and socket of the smaller one have a greater difference. In this way, it is possible to produce a tapered bracket which has a generally uniform resistance to articulation along its length, and is just as strong as, but lighter in weight and less obtrusive than, one made up of elements of uniform size.

The most important features of the supporting bracket is the interference fit of the balls and sockets, and the significant area of contact between them, which together provide the rigidity necessary for tissue stabilization in heart surgery. These features also allow the bracket to be adjusted easily and locked into its rigid condition by the application of a moderate force on the cable.

Modifications can be made to the supporting bracket shown and described. For example, whereas the bracket shown has three sets of five elements, one set of three elements, and three transition elements, and the elements of each of the four sets are all identical, it is possible to use other numbers and arrangements of elements. The configurations of the elements can be modified as well. For example, the elements can be either longer or shorter than the elements shown. The cable tensioner 16 can utilize various arrangements of screws and/or levers, and the distal end clamping assembly can use any of a wide variety of alternative devices for holding the shank of the tissue stabilizer or for holding another device.

Still other modifications may be made to the apparatus and method described above without departing from the scope of the invention as defined in the following claims.

We claim:

1. A supporting bracket comprising a first end element having a convex, spherical surface, a second end element having a concave, spherical surface, and a plurality of intermediate elements each intermediate element having first and second ends, with a convex, spherical surface at the first end and a concave, spherical surface, defined by a wall, at the second end, in which each convex spherical surface is in mating relationship with the concave spherical surface of another of said elements, in which each element has a passage, and having a cable extending through the passages, and means for tightening the cable and thereby causing the convex spherical surfaces to be brought into tight frictional engagement with their mating concave spherical surfaces, in which each convex, spherical surface has an outer diameter larger than the relaxed internal diameter of its mating concave spherical surface, and in which the wall defining each concave, spherical surface is sufficiently flexible to permit it to be brought into concentric relationship with the convex spherical surface with which it is in mating relationship, with the concentric mating surfaces in area contact with each other.

2. A supporting bracket according to claim 1 in which the outer diameter of each convex, spherical surface exceeds the relaxed internal diameter of its mating concave spherical surface by an amount in the range of approximately 0.001 to 0.002 inches.

3. A supporting bracket according to claim 1 in which the outer diameter of each convex, spherical surface exceeds the relaxed internal diameter of its mating concave spherical surface by an amount in the range of approximately 0.0015 to 0.002 inches.

4. A supporting bracket according to claim 1 in which, for each mating pair of concave and convex spherical surfaces, the concave spherical surface extends substantially from a first circle, which is concentric therewith, to a first end opening of the passage in the corresponding element, said first end opening having a perimeter;

the convex spherical surface extends substantially to a second circle adjacent to an end opening of the passage in the corresponding element; and the area of contact of the mating pair of convex and concave spherical surfaces, when in concentric relationship and with the elements having said mating pair of surfaces tilted relative to each other, extends substantially from said first circle to an envelope in the form of the outline of two intersecting circles, said envelope being defined by the perimeter of said first end opening and said second circle.

5. A supporting bracket according to claim 1 in which the convex spherical surface of at least one of the intermediate elements has a diameter different from that of its concave spherical surface.

6. A supporting bracket according to claim 1 in which the convex spherical surface of at least one of the intermediate elements has a diameter greater than that of its concave spherical surface.

7. A supporting bracket according to claim 1 in which the diameter of the convex, spherical surface of the first end element is different from that of the concave, spherical surface of the second end element, and in which the sizes of the convex spherical surfaces of the intermediate elements decreases in steps, proceeding along the intermediate elements in a direction from one of the end elements toward the other.

8. A supporting bracket according to claim 1 in which the diameter of the convex, spherical surface of the first end element is different from that of the concave, spherical surface of the second end element, in which the sizes of the convex spherical surfaces of the intermediate elements decreases in steps, proceeding along the intermediate elements in a direction from one of the end elements toward the other, and in which the difference between the outer diameter of each convex spherical surface and the relaxed internal diameter of its mating concave spherical surface, increases progressively as the sizes of the convex spherical surfaces of the intermediate elements decrease.

9. A supporting bracket according to claim 1 in which intermediate elements comprise a first set of successively arranged intermediate elements, each element of the first set having the diameter of its convex spherical surface approximately equal to the diameter of its concave spherical surface, a second set of successively arranged intermediate elements, each element of the second set having the diameter of its convex spherical surface approximately equal to the diameter of its concave spherical surface, the diameters of the convex and concave spherical surfaces of the elements of the second set being different from the diameters of the convex and concave spherical elements of the first set, and a transition element connecting an element of the first set to an element of the second set, the transition element having a convex spherical surface mating with a concave spherical surface of an element of the first set, and a concave spherical surface mating with a convex spherical surface of an element of the second set.

10. A supporting bracket according to claim 1 in which the passage of each intermediate element comprises a first section extending from a first end opening in the convex spherical surface thereof to an intermediate location, and a second section extending from the intermediate location to a second end opening in the concave spherical surface thereof, and in which the first section is gradually flared from a location adjacent to said intermediate location to the first end opening.

11. A supporting bracket according to claim 10 in which each intermediate element is in adjoining relationship with at least one other intermediate element to constitute an articulating pair of elements, in which each articulating pair of elements has means for limiting the its articulation, and in which the sizes of the end openings of the passages in the mating concave and convex spherical surfaces of each articulating pair of elements are sufficiently large that, even when the elements of the articulating pair are at their limit of articulation, they provide a passage through which the cable can move freely.

12. A supporting bracket according to claim 1 in which the contact area of the mating spherical surfaces is at least approximately 20% of the total surface area of a corresponding sphere.

13. A supporting bracket according to claim 12 in which the passage of each said element having a convex, spherical surface has a rounded end opening in the convex spherical surface thereof.

14. A supporting bracket according to claim 1 in which the contact area of the mating spherical surfaces is at least approximately 30% of the total surface area of a corresponding sphere.

15. A supporting bracket according to claim 1 in which the contact area of the mating spherical surfaces is approximately 30% to 40% of the total surface area of a corresponding sphere.

* * * * *